United States Patent [19]

Lindstrom

[11] Patent Number: 5,140,981
[45] Date of Patent: Aug. 25, 1992

[54] END-TIDAL GAS DETECTION

[75] Inventor: Walter W. Lindstrom, Shaker Hts., Ohio

[73] Assignee: Picker International, Inc., Highland Hts., Ohio

[21] Appl. No.: 275,784

[22] Filed: Nov. 23, 1988

Related U.S. Application Data

[63] Continuation-in-part of Ser. No. 933,781, Nov. 24, 1986, Pat. No. 4,793,357.

[51] Int. Cl.$^5$ ............................................. A61M 16/00
[52] U.S. Cl. .............................. 128/203.25; 128/654; 128/719
[58] Field of Search ............ 128/654, 659, 719, 204.18, 128/203.12, 203.25

[56] References Cited

U.S. PATENT DOCUMENTS

| | | | |
|---|---|---|---|
| 3,890,959 | 6/1975 | Youdin et al. | 128/654 |
| 4,535,780 | 8/1985 | Gur et al. | 128/659 |
| 4,622,976 | 11/1986 | Timpe et al. | 128/654 |
| 4,718,432 | 1/1988 | Kimura et al. | 128/654 |
| 4,779,621 | 10/1988 | Mattson | 128/654 |

FOREIGN PATENT DOCUMENTS 3522113 1/1986 Fed. Rep. of Germany.

OTHER PUBLICATIONS

"Simultaneous Mass Spectrometry and Thermoconductivity ... " by Gur, et al., Med. Phys. 11(2) Mar./Apr. 1984, pp. 209–212.

"Progress in Cerebrovascular Disease" by Gur, et al., Stroke, vol. 13, No. 6, 1982, pp. 750–758.

"Experimental Xenon Enhancement with CT Imaging: Cerebral Applications" by Drayer, et al., AJR, 134:39–44, Jan. 1980.

European Search Report dated Feb. 12, 1990.

Primary Examiner—Edgar W. Burr
Assistant Examiner—Aaron J. Lewis
Attorney, Agent, or Firm—Fay, Sharpe, Beall, Fagan, Minnich & McKee

[57] ABSTRACT

A patient breathing through a mask (34) receives breathing air from a breathing air system (A). A xenon gas supply (12) selectively supplies xenon or other enhancement gases into the breathing air. During each exhalation portion of a respiratory cycle, a portion of the exhaled gas passes through a narrow tube (40) to a xenon concentration detector (44) and a carbon dioxide concentration detector (46). A carbon dioxide concentration comparing circuit (54) compares the carbon dioxide concentration values with characteristics (56) of carbon dioxide concentration during an end-tidal portion of the exhalation respiratory cycle. Xenon concentrations read during the end-tidal portion of the respiratory cycle (62) are utilized to project a blood absorption curve (64). A plurality of CT images are generated by a CT scanner (B) as the blood xenon concentration increases. A look-up table array (90) preprogrammed in accordance with the Kety equations is addressed by the blood xenon concentration curve and the pixel values of the CT images to generate partition coefficient and flow values.

17 Claims, 3 Drawing Sheets

END-TIDAL GAS DETECTION

The present application is a continuation in part of U.S. application Ser. No. 933,781, filed Nov. 24, 1986, now U.S. Pat. No. 4,793,357.

BACKGROUND OF THE INVENTION

The present invention relates to the art of medical diagnostic equipment. It finds particular application in conjunction with measuring xenon concentration in end-tidal gases. However, it is to be appreciated that the invention will also find application in conjunction with measuring concentrations of other gases.

Many medical diagnostic techniques call for a measurement of an absorbed gas in the patient's blood. Arterial blood gas concentration are in equilibrium with lung gases that are in intimate contact with the alveoles. These lung gases, denoted as end-tidal gases, are found at the end of the tide of the exhaled breath. By measuring the concentration of the gas in question in these last bits of the exhaled gas, the concentration of the gas in the blood can be determined.

The xenon concentration in the end-tidal gas can be measured by placing a thermoconductivity detector in the exhalation line. See U.S. Pat. No. 4,622,976, issued Nov. 18, 1986 to G. M. Tempe, et al., which measures xenon concentration, carbon dioxide concentration, or the like. Because the thermoconductivity detector will indicate xenon concentration continuously, it was necessary to determine which reading represents the end-tidal gases.

In one end tidal identifying technique, a chamber or reservoir was formed in the exhaled gas line leading from the breathing mask to hold exhaled gas. A mechanical system determined when the patient started to inhale fresh gas from a supply line. The thermoconductivity of the gas retained in the exhale chamber was measured. See for example U.S. Pat. No. 4,535,780, issued Aug. 20, 1985, to Gur, et al. One of the problems of this technique is that the apparatus is expensive. Another problem is that the mechanical means for determining the changeover point between inhaling and exhaling tends to be relatively unreliable. Another disadvantage is that exhaled gases intermix in the chamber diluting the end-tidal gases with earlier exhaled gases.

Another technique for determining the end-tidal gas was to monitor the xenon concentration continuously and assume that the xenon concentration minima were attributable to the end-tidal gases. However, when the patient began breathing rapidly, the minimum xenon concentrations did not correspond to end-tidal gas. Further, after the first few patient breaths, the magnitudes of the minima increased sufficiently close to the breathing gas xenon concentration that they were difficult to identify. Commonly, the end-tidal gas minimum values became substantially indistinguishable from the exhaled xenon concentration in the rest of the exhaled gas after the first minute of a five to seven minute xenon protocol.

The present invention provides a technique for determining end-tidal gases which overcomes the above referenced problems and others.

SUMMARY OF THE INVENTION

In accordance with one aspect of the present invention, a method for determining enhancement agent, e.g. xenon concentrations, in end-tidal gases is provided. The concentration of carbon dioxide in the exhaled gases is monitored and compared with preselected characteristics. In response to the comparison, an enhancement gas concentration is read. In this manner, the carbon dioxide gas concentration is utilized to identify the end-tidal gases whose enhancement agent concentration is to be measured.

In accordance with another aspect of the present invention, an apparatus for measuring blood enhancement gas concentrations is provided. A breathing mask is connectable with sources of breathing air and enhancement gas. Carbon dioxide and xenon concentration analyzing means are connected with the mask for measuring concentrations of carbon dioxide and enhancement gas in exhaled gases. A comparing means compares the carbon dioxide concentration readings with preselected characteristics and causes the enhancement gas concentration analyzing means to measure a end-tidal enhancement gas concentrations.

In accordance with more limited aspects of the present invention, the above described method is performed in conjunction with a xenon enhanced medical diagnostic imaging procedure.

In accordance with another more limited aspect of the present invention, the above described apparatus is combined with a medical diagnostic imaging apparatus, such as a CT scanner.

One advantage of the present invention is that it accurately identifies end-tidal gases. The present invention even identifies respiratory cycles in which the exhale period ends before end-tidal gases are exhaled.

Another advantage of the present invention is that it is relatively inexpensive.

Another advantage of the present invention is that it reduces dilution of the end-tidal gases.

Still further advantages of the present invention will become apparent to those of ordinary skill in the art upon reading and understanding the following detailed description.

BRIEF DESCRIPTION OF THE DRAWINGS

The invention may take form in various steps and arrangements of steps or in various parts and arrangements of parts. The drawings are only for purposes of illustrating a preferred embodiment and are not to be construed as limiting the invention.

DETAILED DESCRIPTION OF THE PREFERRED EMBODIMENT

Figure 1A:
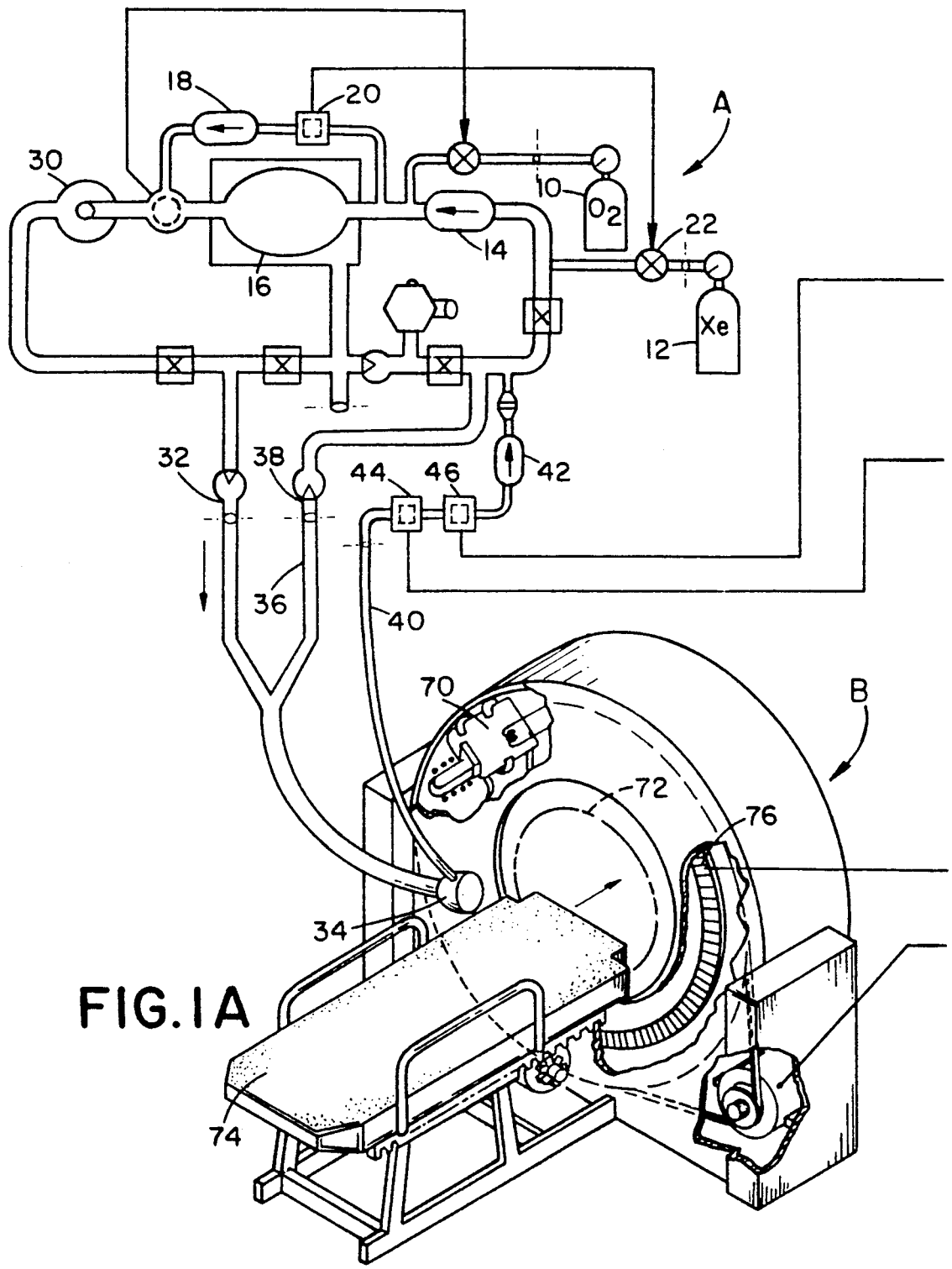
FIGS. 1A and 1B taken together are a diagrammatic illustration of a CT scanner in combination with a blood xenon gas concentration measuring system in accordance with the present invention.
Figure 1B:
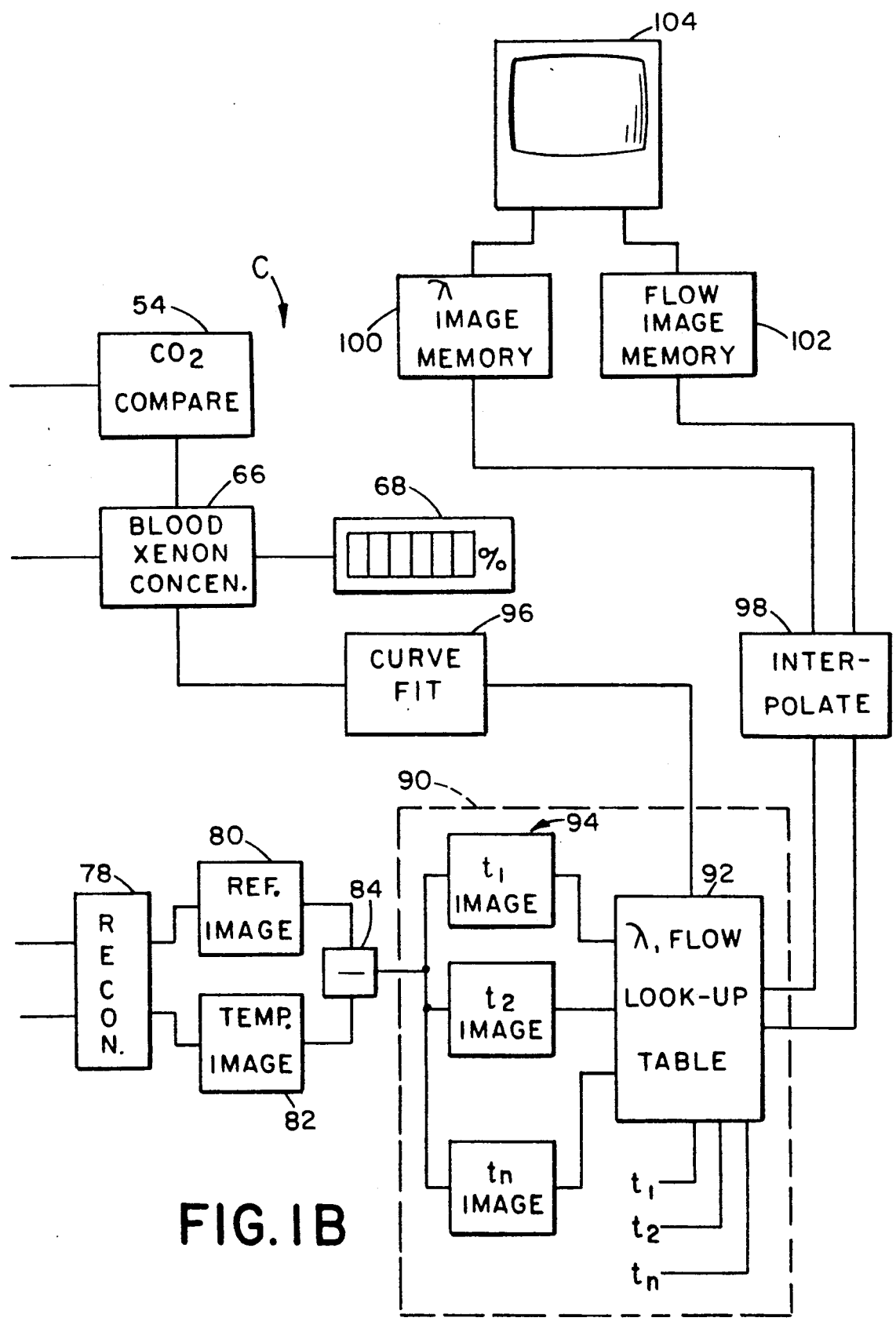

With reference to FIGS. 1A and 1B, a gas supply means A supplies breathing gas to a medical diagnostic scanner such as a CT scanner B. A processing system or means C processes data from the CT scanner and the breathing gas supply system to produce images and other diagnostic information.

The breathing gas supply means A includes a breathing air or oxygen supply 10 and a xenon gas supply 12.

Preferably, the xenon gas supply means provides a mixture of 80% xenon and 20% oxygen to guarantee that the patient receives at least 20% oxygen even during a malfunction. A first blower 14 supplies recirculated breathing gases along with added xenon for mixture with additional oxygen from the oxygen supply means 10. Most of the mixture passes to a breathing bag 16 with the exception of a small fraction that is pumped by a pump 18 through a xenon detector 20. The xenon detector 20 determines the concentration of xenon in the gaseous breathing mixture and controls a xenon control valve 22 to maintain the xenon concentration substantially constant. Typically, the xenon concentration is selected to be about 30%.

A carbon dioxide absorber 30 removes carbon dioxide from the breathing gases that are supplied to an outlet port check valve 32. When the patient inhales through a breathing mask 34, the patient draws the breathing gases through the outlet check valve 32. When the patient exhales, the exhaled gases are returned through an exhaust gas path or tube 36 and a return check valve 38. The exhaust gases passing through the return check valve 38 are returned to the blower 14 and recirculated through the system.

The exhaust gas analysis is performed periodically, e.g. every 0.25 seconds, on gases passing through a small diameter line 40 extending parallel to the exhaust gas path to reduce the dilution effects. In the much larger diameter exhaust gas path, the exhaust gases tend to tumble and mix which dilutes end-tidal gases with other exhaust gases. The narrow diameter line inhibits the swirling and countercurrent flow patterns that tend to intermix the gases and enables a more nearly instantaneous reading of the gases to be made. The gases drawn through the small diameter line by a pump or blower 42 are analyzed by a xenon detector 44 and a carbon dioxide detector 46. The xenon detector measures the xenon concentration of the exhaled gases and the carbon dioxide detector measures the carbon dioxide concentration of the exhaled gases.

Figure 2:
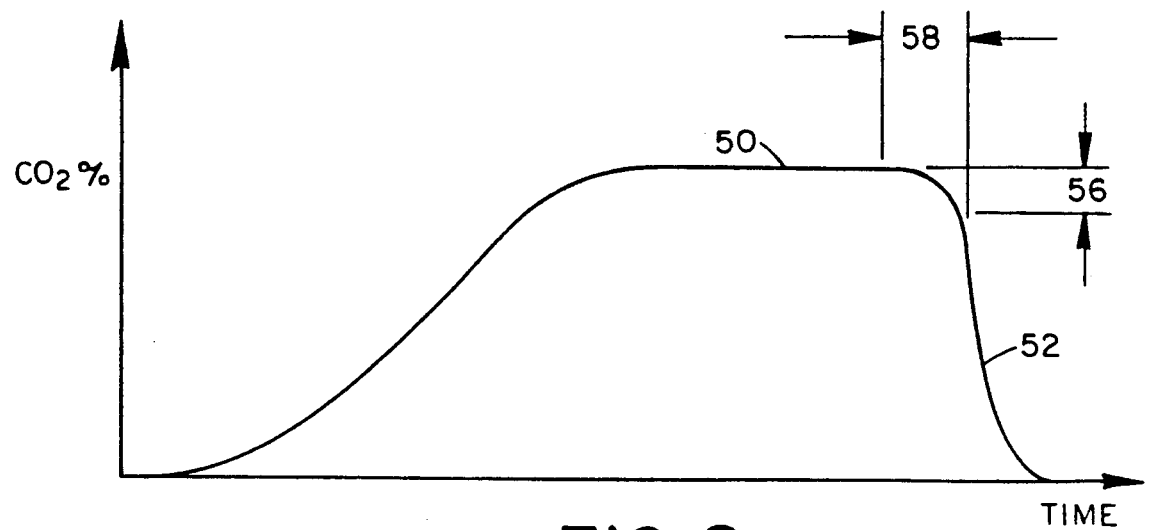
FIG. 2 illustrates a typical $CO_2$ concentration vs. time for a single breathing cycle with the trigger point for the xenon gas concentration reading in accordance with the present invention indicated; and, FIG. 3 illustrates exhaled gas xenon concentration vs. time over multiple breathing cycles following initiation of xenon delivery to the patient.

With particular reference to FIG. 2, as the patient starts to exhale, the concentration of carbon dioxide gas increases generally exponentially and logarithmically to a plateau 50. The carbon dioxide concentration remains relatively constant through a significant portion of the exhalation portion of the respiratory cycle. Just after the end-tidal gases are exhaled, the patient inhales $CO_2$ free gas through check valve 32 and the $CO_2$ concentration drops rapidly 52. A carbon dioxide level comparing means 54 compares the carbon dioxide level with preselected characteristics, specifically, a preselected drop 56 from the plateau 50. In response to the preselected carbon dioxide concentration drop, the comparing means 54 triggers the selection of a previously taken end-tidal xenon concentration reading by the xenon detector 44 a fixed, preselected time earlier 58, e.g. a 0.5 sec.

With continuing reference to FIG. 2, when the patient is panting rapidly, end-tidal gas is not reliably discharged at the end of the exhalation cycle. Accordingly, it may be advantageous not to sample the xenon concentration detector 44 in a panting respiratory cycle. However, the partial pressure of $CO_2$ during panting does not rise to the plateau concentration 50. Hence, the measured drop 56 from the plateau does not occur and the sampling of blood xenon concentration is not triggered.

Figure 3:
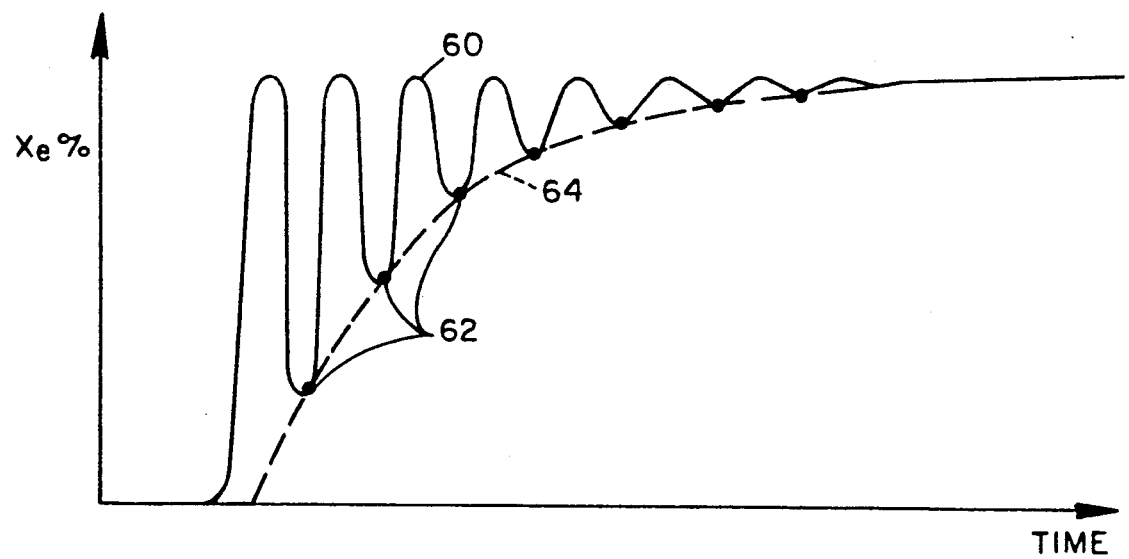

With reference to FIG. 3, in each respiratory cycle, the concentration of xenon gas peaks 60 at the xenon concentration in the breathing air. In an exhale cycle portion in which the patient's lungs are fully evacuated such that end-tidal gas is expelled, the xenon concentration reaches a minimum value 62 at the end-tidal portion of each breath. The blood xenon concentration and the corresponding end-tidal xenon concentration increase along a blood xenon absorption curve 64. However, with several respiratory cycles, the concentration of xenon in the patient's blood approaches the concentration of xenon in the breathing gas. After a half dozen or a dozen breaths, the differences in height between the xenon concentration peaks and valleys becomes so small that the random noise fluctuations cannot reliably be differentiated from the true xenon concentration minimum.

The end-tidal xenon concentrations 62 are conveyed to a blood xenon concentration curve memory means 66. A blood xenon concentration display means 68 is connected with the blood xenon concentration memory means to provide the physician with a continuous indication of blood xenon concentrations. The output of this memory means may also be displayed as a graph of xenon or blood xenon concentration vs. time.

The CT medical diagnostic scanner B of the preferred embodiment includes an x-ray source 70 for projecting a fan beam of radiation through an image region 72. The patient is supported on a patient table 74 with tissue to be examined, typically the head or brain tissue, disposed in the image region. An array of x-ray detectors 76 receives the fan beam of radiation from the x-ray source including the radiation which has traversed the portion of the patient from the image region. An image reconstruction means 78 reconstructs CT image representations from the x-ray data collected by the radiation detectors as the radiation source is rotated about the region of interest.

The processing circuitry C includes a reference image means 80 for storing an image representation of the tissue of interest of the patient without xenon gas absorbed in the patient's blood. As the patient starts inhaling xenon containing gas and the patient's blood xenon concentration increases, several additional CT images are taken, each being stored temporarily in an image memory 82. Each image can be considered as the sum of a patient tissue image and a xenon image. A subtraction means 84 subtracts the reference image from each subsequent image to produce a difference image indicative of xenon concentrations. More specifically, each difference image includes an array of pixel values, each pixel value corresponding to a preselected volume cell (voxel) or subregion of the portion of the patient disposed in the image region.

A partition coefficient and blood flow rate determining means 90 utilizes known relationships, such as the relationships set forth in the Kety equation, to determine a partition coefficient and blood flow rate for each image voxel. These calculations are based on the blood xenon concentration curve stored in the blood xenon concentration in memory 66 and the increase in xenon concentration in subsequent corresponding pixels of the difference image. In the preferred embodiment, the partition coefficient and blood flow values are determined on a pixel by pixel basis from a look-up table means 92. The look-up table means is addressed by the relative times $t_1$, $t_2$, $t_n$ of the CT scans, corresponding pixel values of a plurality of CT scans as stored in difference scan memories 94, and by blood xenon concentration curve parameters. More specifically, a blood xenon concentration parameter determining means 96 determines conformity of the actual blood xenon concentration curve to preselected concentration curve characteristics, such as saturation concentration, slope, exponential time constants, and the like. In one embodiment, the look-up table means includes an array of look-up tables. The blood xenon concentration curve characteristics determine which look-up table(s) conforms best to the patient blood xenon concentration curve. The selected look-up table(s) is then addressed by the corresponding pixel values from each image in the difference image memory means 94. The relative times at which the images were collected in the preferred embodiment are preset. However, if the times are to be variable, these times are also utilized to select among a larger plurality of look-up tables.

Digital look-up tables can only be addressed by preselected addresses. The actual pixel values may fall between these addresses. Each of the two closest addresses are accessed and an interpolating means 98 performs a weighted interpolation of the retrieved partition coefficient and flow values. Analogously, the absorption curve characteristics may fall between two or more look-up tables of the array. An interpolation means 98 performs a weighted interpretation of the partition coefficient and flow values retrieved by the closest difference image pixel values and the closest time or xenon curve addressed look-up tables.

The procedure is repeated for each pixel of the images to build a partition coefficient image for storage in a partition coefficient image memory 100 and a flow image for storage in a flow image memory means 102. The partition coefficient and flow images may be selectively displayed on a display means 96. Optionally, other parameters may also be displayed, such as a confidence or fit value which is indicative of how closely each partition coefficient and flow value conforms with the normal statistical deviation from the actual value, i.e. reliability or confidence that one may have in each pixel value.

The invention has been described with reference to the preferred embodiment. Obviously, modifications and alterations will become apparent to those of ordinary skill in the art upon reading and understanding the preceding specification. It is intended that the invention be construed as including all such alterations and modifications insofar as they come within the scope of the appended claims or the equivalents thereof.

Having thus described the preferred embodiments, the invention is now claimed to be:

1. A method for measuring concentration of a preselected gaseous component other than carbon dioxide of end-tidal gases from a patient, the method comprising:
    providing a patient with breathing gases
    measuring carbon dioxide concentrations in exhaled gas during at least exhalation portions of a respiratory cycle;
    monitoring carbon dioxide concentration in exhaled gases for a preselected criteria indicative of a decrease from a respiratory cycle carbon dioxide concentration maximum, which decrease is indicative of when end-tidal gases are exhaled; and,
    measuring the concentration of the preselected gaseous component in direct response to the monitoring of the preselected criteria indicating the end-tidal gas exhalation point of the respiratory cycle such that the concentration of the preselected gaseous component in the end-tidal gases is measured.

2. The method as set forth in claim 1 further including repeating the carbon dioxide measuring, comparing, and preselected gaseous component measuring steps over each of a plurality of respiratory cycles as a concentration of the preselected gaseous component in a patient's blood increases to generate points of a curve indicative of changes in the preselected gaseous component in the patient's blood over time.

3. The method as set forth in claim 1 wherein during an exhalation portion of each respiratory cycle, the monitored carbon dioxide concentration increases to a plateau concentration and decreases rapidly from the plateau at the end-tidal portion of the respiratory cycle and wherein the comparing step includes determining a preselected fall-off from the plateau, selecting a measurement of the preselected gaseous component taken a preselected duration prior to the occurrence of the preselected fall-off.

4. The method as set forth in claim 3 wherein the preselected gaseous component is xenon.

5. The method as set forth in claim 4 further including storing each measured end-tidal xenon concentration and determining characteristics of at least one curve which describes variations in the measured xenon concentration with time.

6. A method for measuring xenon gas concentration in end-tidal gases from a patient, the method comprising:
    providing a patient with breathing gases
    measuring concentrations of carbon dioxide in exhaled gas during at least end-tidal exhalation portions of a respiratory cycle;
    monitoring carbon dioxide concentration in an exhaled gas for a decrease from a respiratory cycle carbon dioxide concentration maximum;
    measuring xenon gas concentration in the exhaled gas
    selecting a xenon gas concentration measured concurrently with the carbon dioxide concentration decrease.

7. A method of measuring partition coefficient and blood flow values of a patient disposed in a diagnostic scanner, the method comprising:
    a) providing the patient with breathing gases;
    b) introducing an enhancement gas into the breathing gases such that a concentration of the enhancement gas in the patient's blood increases with time;
    c) measuring carbon dioxide concentrations in gases exhaled by the patient;
    d) comparing the measured carbon dioxide concentration in exhaled gases for a preselected criteria indicative of a carbon dioxide concentration decrease from a respiratory cycle carbon dioxide maximum;
    e) in response to determining that the carbon dioxide concentration decrease indicative of end-tidal gases has occurred, measuring the enhancement gas concentration in the exhaled breathing gases;
    f) repeating steps (c) to (e) over a plurality of respiratory cycles to generate a blood enhancement gas concentration curve;
    g) also over the plurality of respiratory cycles, generating a plurality of diagnostic images in which the enhancement agent concentration changes from image to image, each diagnostic image including a plurality of pixel values; and,
    h) calculating partition coefficient and blood flow values from the blood enhancement gas concentration curve and at least selected corresponding pixel values of the series of images.

8. The method as set forth in claim 7 further including repeating the carbon dioxide measuring, comparing, and preselected gaseous component measuring steps over each of a plurality of respiratory cycles as a concentration of the preselected gaseous component in a patient's blood increases to generate points of the blood enhancement gas concentration curve indicative of changes in the preselected gaseous component in the patient's blood over time.

9. A method of measuring partition coefficient and blood flow values of a patient disposed in a diagnostic scanner, the method comprising:
   (a) providing the patient with breathing gases;
   (b) introducing an enhancement gas into the breathing gases such that a concentration of the enhancement gas in the patient's blood increases with time;
   (c) monitoring breathing gases exhaled by the patient for carbon dioxide concentration, during an exhalation portion of each respiratory cycle, the monitored carbon dioxide concentration increases to a plateau and decreases rapidly from the plateau at the end-tidal portion of the respiratory cycle;
   (d) determining a preselected decrease of the measured carbon dioxide concentration from a plateau said decrease being indicative of carbon dioxide concentration fall-off in end-tidal gases;
   (e) in response to the occurrence of the preselected fall-off, measuring the enhancement gas concentration in the exhaled breathing gases;
   (f) repeating steps (c) to (e) over a plurality of respiratory cycles to generate a blood enhancement gas concentration curve;
   (g) also over the plurality of respiratory cycles, generating a plurality of diagnostic images in which the enhancement agent concentration changes from image to image, each diagnostic image including a plurality of pixel values; and,
   (h) calculating partition coefficient and blood flow values from the blood enhancement gas concentration curve and at least selected corresponding pixel values of the series of images.

10. The method as set forth in claim 9 wherein the enhancement gas component is xenon.

11. The method as set forth in claim 10 further including storing each measured end-tidal xenon concentration and determining characteristics of at least one curve which describes variations in the measured xenon concentration with time.

12. A medical diagnostic apparatus comprising:
   a breathing mask means through which a patient inhales breathing gas and exhales exhalation gases;
   a breathing gas supply means for supplying breathing gas to the mask means;
   an enhancement gas introduction means for selectively introducing an enhancement gas into the breathing gas;
   a carbon dioxide analyzing means for measuring carbon dioxide concentration, the carbon dioxide analyzing means being operatively connected with the mask means to receive at least exhalation gases therefrom;
   a carbon dioxide concentration comparing means for comparing the measured carbon dioxide concentration with characteristics of a decrease from a carbon dioxide concentration maximum, said decrease being indicative of end-tidal gases;
   an enhancement gas analyzing means for measuring enhancement gas concentration, the enhancement gas analyzing means being operatively connected with the mask means to receive at least exhalation gases therefrom; and
   an end-tidal enhancement gas concentration record means operatively connected with the enhancement gas analyzing means and the comparing means for providing a record of end-tidal enhancement gas concentrations said analyzing means, said comparing means and said record means being directly responsive to said carbon dioxide concentration decrease.

13. The apparatus as set forth in claim 12 wherein the breathing gas supply means receives the exhalation gases from the breathing mask through an exhalation gas outlet port and further including gas conditioning means for conditioning the exhalation gases before being supplied to the breathing mask with the breathing gases.

14. The apparatus as set forth in claim 13 further including a further breathing gas return passage extending from the breathing mask to the breathing air system, the enhancement gas and carbon dioxide detector means being connected along the return path, the return path being smaller in diameter than the exhalation gas outlet, whereby mixing and dilution of gases monitored by the carbon dioxide and enhancement gas detector means is inhibited.

15. The apparatus as set forth in claim 12 further including a medical diagnostic imaging means for taking a plurality of medical diagnostic images through a region of interest of a patient breathing through the breathing mask as a concentration of the enhancement gas increases.

16. The apparatus as set forth in claim 12 further including a xenon gas supply means for selectively supplying xenon gas to the breathing gas, whereby the enhancement gas is xenon.

17. The apparatus as set forth in claim 16 further including:
   a CT scanner means for generating a plurality of diagnostic images through a region of interest of a patient breathing through the breathing mask;
   a partition coefficient and blood flow rate determining means for determining partition coefficient and blood flow rates for subregions of the region of interest from the CT images and the end-tidal xenon concentrations.

* * * * *